(12) United States Patent
Logue et al.

(10) Patent No.: US 6,265,871 B1
(45) Date of Patent: Jul. 24, 2001

(54) DEVICE FOR GENERATING EDDY CURRENT INDUCTION AND DETECTION BY MEANS OF THE AXES OF PERMEABILITY WITHIN A TOROID/TORUS CORE

(75) Inventors: Delmar L. Logue, Herrick; Stephen J. Logue, Taylorville, both of IL (US)

(73) Assignee: Logue Sensor Co., Herrick, IL (US)

( * ) Notice: Subject to any disclaimer, the term of this patent is extended or adjusted under 35 U.S.C. 154(b) by 0 days.

(21) Appl. No.: 09/467,599

(22) Filed: Dec. 20, 1999

Related U.S. Application Data

(63) Continuation-in-part of application No. 09/138,750, filed on Aug. 24, 1998, now Pat. No. 5,399,778, and a continuation-in-part of application No. 09/419,140, filed on Oct. 15, 1999.

(51) Int. Cl.[7] ............................ G01R 33/12; G01N 27/72
(52) U.S. Cl. ............................................. 324/240; 324/242
(58) Field of Search .................................. 324/240, 239, 324/242, 234, 233, 232, 262

(56) References Cited

U.S. PATENT DOCUMENTS 5,532,591 * 7/1996 Logue .................................. 324/242

* cited by examiner

Primary Examiner—Walter E. Snow

(57) ABSTRACT

A single toroidal core is wound with excitation/detection windings for reciprocal-integral eddy current driving-detection means, the pick-up coil being wound around the circumference of the toroid core. The utilized fields being orthogonal for an inherent null. The preferred excitation is ramping sine-cosine currents generating a variable angular velocity driving dipole. A rotating field torus core having an excited poloidal winding for generating concentric n-s s-n diameter-wise dipoles on the plane of the torus for shifting the hemispherical sensing field eccentric in an orbital motion.

4 Claims, 2 Drawing Sheets

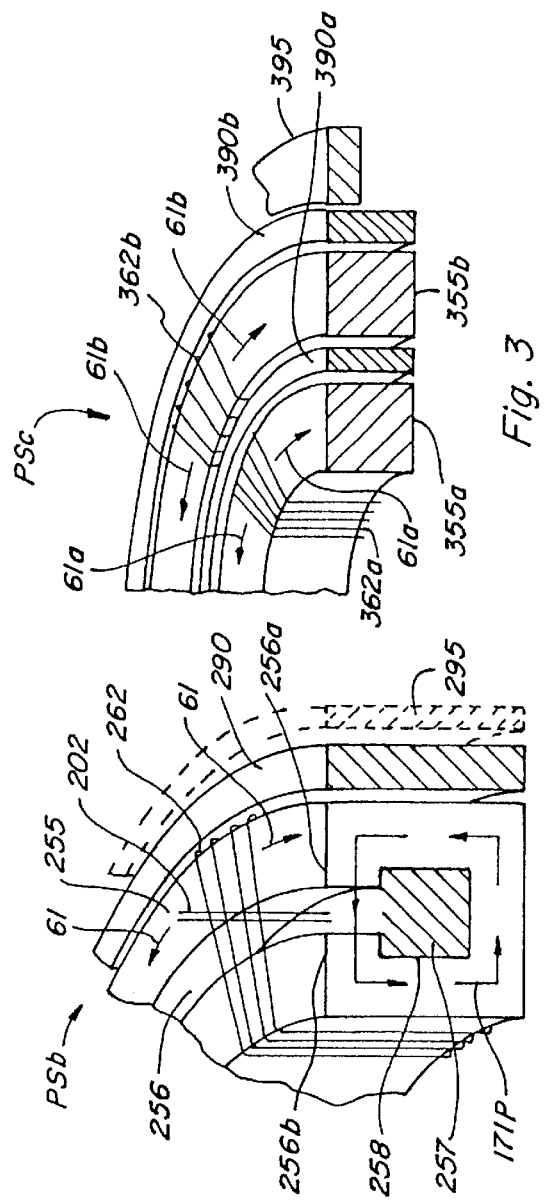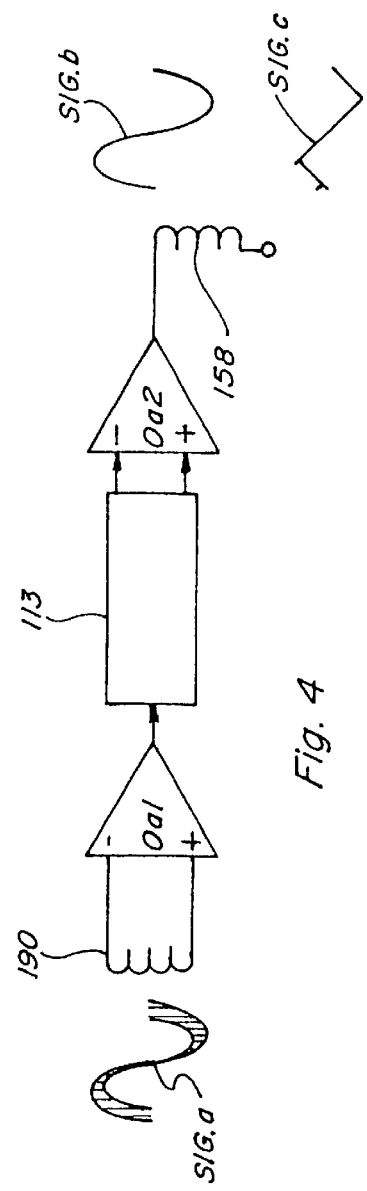

DEVICE FOR GENERATING EDDY CURRENT INDUCTION AND DETECTION BY MEANS OF THE AXES OF PERMEABILITY WITHIN A TOROID/TORUS CORE

CROSS-REFERENCE TO RELATED APPLICATIONS

This Patent Application is a continuation-in-part of patent application Ser. No. 09/138,750 filed Aug. 24, 1998, now U.S. Pat. No. 5,399,778, and Ser. No. 09/419,140 filed Oct. 15, 1999. The concepts of this invention were originally filed.

BACKGROUND ART

Tesla U.S. Pat. No. 382,280 disclosed a ring built up of thin insulated annular iron plates and wound with poly-phase distributions forming an early rotating field stator for generator/motor use. Field utility was limited to the cylindrical window of the stator. Tomsk Poly Eltin In 09.06.86-SU-099729patent disclosed a device utilizing the cited Tesla stator for detecting flaws in long cylindrical objects. Eddy current induction was limited to the toroid window location.

Copending Logue patent Ser. No. 09/138,750 filed Aug. 24, 1998 disclosed a new use for the cited Tesla stator wherein the rotating hemispherical flux fringing from the plane of the toroidal stator was utilized for inducing eddy currents.

The objectives of the invention is utilization of all the known axes of permeability generated within a single toroid core for providing both driving and pick-up fields. A majority of these axes are utilized reciprocally for extending eddy current generation/detection. Also a majority of these axes are orthogonal to each other providing integral flux circuits and inherent nulling. A torus is simply a toroid with approximately ⅙ of the cross-section removed. Further, the poloidal flux circuit in a torus rotates around an axis which is in a horizonal plane.

Logue U.S. Pat. No. 5,793,204 "Method for Generating a Rotating Elliptical Sensing Pattern" introduced dynamic driving flux modulation as a means for increasing spatial resolution. To further this objective, this disclosure teaches a dynamic poloidal axis modulation to generate an orbital motion to the sensing pattern. Eccentricity is vectorially added to the sine-cosine excited rotating induction vector.

Dual rotating driving cores were introduced in Logue U.S. Pat. No. 5,754,043 coupled to concentric pick-up cores and coils. Separate poly-phase excitation generators controlled individual angular velocity. In a further version of the invention, a plurality of toroids concentrically interposed with pick-up coils on different radii provides a similar eddy current patterns.

An axis of permeability is defined in this disclosure as a cross-section of magnetic material conducting a dipole of magnetic force. This cross-section may take the form of a cylinder (z-axis), a circle (toroidal-axis), torus (poloidalaxis) or diameter-wise (x-y axes).

The Invention

The effective lines of force fringing from the magnetic circuits utilized may best be viewed in global geometry.

The primary object of the invention is the utilization of a single toroidal core generating both driving and sensing fields for eddy current flaw evaluation. This toroid core is wound to have inherent orthogonality between the axes of induction (vectorial sum of axes not exceeding saturation). Additionaly, any of the prior art Logue polar coordinates sensor pick-up assemblies e.g. pot core half, sensing array and the resonator (disclosed in Ser. No. 09/319,140) all, may be concentrically mounted within the toroid window for generating signal/s. Obviously, a torus core can generate a toroidal field.

BRIEF DESCRIPTION OF THE DRAWINGS

FIG. 2 is an arcuate portion of a toroicidal core of the invention showing a groove cross-section for winding a poloidal winding.

FIG. 3 is an arcuate portion of concentric toroid cores utilizing both driving and sensing axes of permeability.

FIG. 4 is a block diagram illustrating a method for adding eccentricity to the sensing pattern.

DESCRIPTION OF THE PREFERRED EMBODIMENTS

Figure 1:
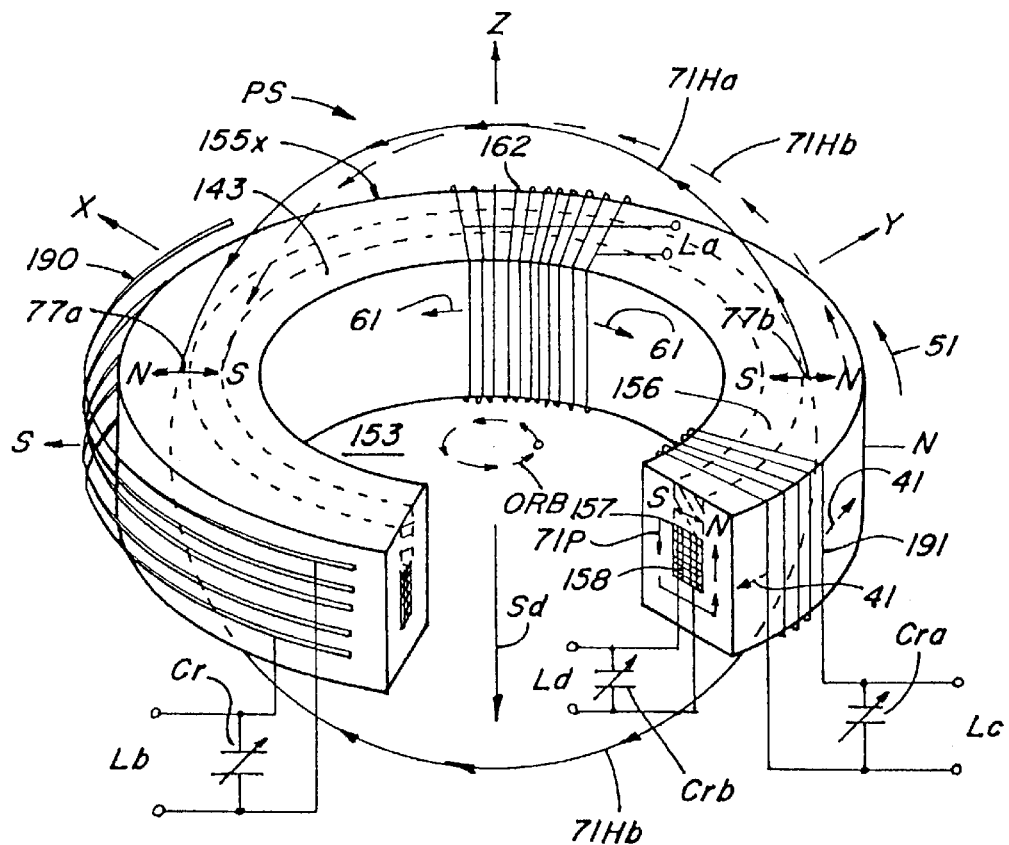
FIG. 1 is a sectional-isometric view of the invention illustrating in composite form a portion of the embodiments.
Figure 1:
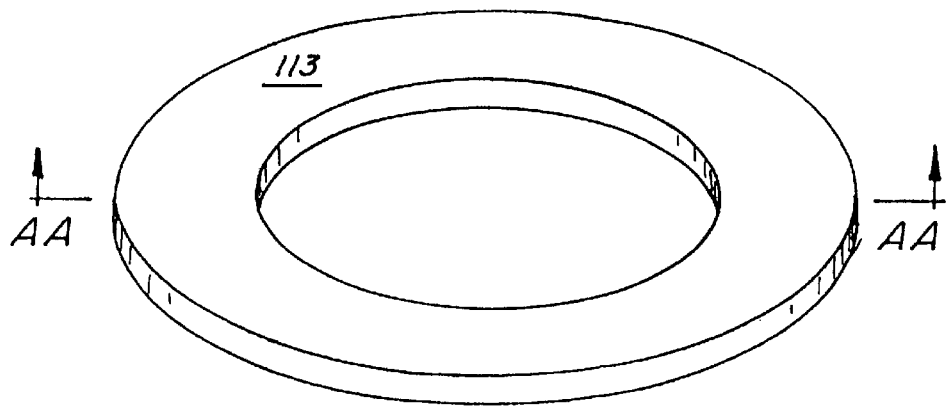

FIG. 1, is a perspective/cross-sectional view of polar sensor PS, which diagrammatically represents a genus of eddy current probes Psa, PSb, PSc . . . .

Core 55x illustrates the global axes of permeability i.e. x-y-z, toroidal and poloidal. Extending this global analogy, the toroidal and poloidal axes have an equatorial location. "Poloidal" is the term used in the DelVecchio U.S. Pat. No. 4,595,843 designating the inside winding 158 of a torus core. Winding 158 may be interchangably used as a driving or a sensing element.

Driver-detector core 155x is formed of a high permeability magnetic material, preferrably tape wound e.g. Supermendur*, Square Orthonol* or Supermalloy* alloys. Polar sensor PS represents all the utilized magnetic circuits (both driving and sensing) are generated within a single core 155x. The dominant driving field i.e. rotating induction vector S←N, is generated by poly-phase windings 162 shuttled through the toroid window 153 (symbolized in partial by coil 162, connected to poly-phase generator by leads La). Sine-cosine excitation windings (complete X-Y distributions are indicated by arrows 61) are preferred. It must be kept in mind, the shown winding 162 represents the sine-cosine embodiment: a) a first pair of parallel distributions of like polarity and, b) a second pair of parallel distributions of like polarity displaced 90 degrees from the first pair. Sine-cosine excitation applied to the said distributions gives angular motion 51 to driving vector S←N, but in a symmetrical flux medium there is no net circulating flux around core 155x. The resultant fringing rotating (arrow 51) driving field globally fills hemispheres 71Ha, 71Hb (solid lines).

A z-axes pick-up coil of many turns (symbolized in partial by windings 190), who's axis is orthogonal to driving vector S←N for an inherent signal null. The major inductance of pick-up coil 190 is the unsaturated magnetic moments integral in stator 155x, whereupon the imbalance flux (flaw) portion of the driving pattern forms a signal dipole Sd on the z-axis. For resonant signal build-up a variable capacitor Cr is connected across connecting leads Lb. Pick-up coil 190 may be wound either over or under excitation windings 162, (this alternate method also applies to pick-up coil 191). The preferred arrangement being, coil 190 wound upon a Nylon spool and disposed over the sine-cosine excitation windings for coplanarity and coaxial adjustments and finally glued in place. A non-conducting fixture for these adjustments is preferred. A toroidal pick-up coil of many turns (symbolized in partial by windings 191, (having complete circumferential coverage indicated by arrows 41). A variable capacitor Cra may be connected across connecting leads Lc for oscillatory signal build-up with ramping poly-phase excitation.

As previously noted, if the sine-cosine excitation winding distributions 162 are spatially in quadat:ure there is no net flux circulaion around core 155x. But nevertheless, toroidal-axis pick-up coil 191 is sensitive to a net global (effective hemispheres 71Ha, 71Hb) flux asymmetry (a flaw). Winding 191 turns should be evenly distributed around driving core 155x for a signal null. For further intergal field utilization a channel (groove) 156 may be formed in the sensing face (top) of toroid 155x for winding a detection/bias coil 158 (poloidal). Toroid winding using different widths of core tape forms a groove in the toroidal sensing face 143. In the detection mode, coil 158 is similar to the pick-up coil wound within the annular space of a pot core half (earlier polar coordinates sensors) having a larger central pole to outer pole diameter ratio. A thick non-ferrous washer 113 formed perferrably of copper may be concentrically disposed in close proximity to the rear end (bottom) of probe PS1 for reflecting the flux toward the sensing face (top). Concentric/eccentric adjustment of washer 113 is also a means of static field balancing, but should be only a very small adjustment.

Oscillatory Signal Build-up

The polar coordinates signal disclosed in the ascending Logue patents is actually formed by successive accelerating revolutions of the driving field imbalance portion linking the pick-up coil and charging an oscillatory tank (the pick-up inductance and capacitor across the pick-up coil/s). This oscillatory signal build-up was first described in Logue U.S. Pat. No. 5,909,118. The resultant accumulative signal is a sub-harmonic of the driving excitation. The present embodiments also generate this oscillatory signal build-up action.

The 1st Embodiment

Integral Driving-sensing in a Single Toroid

Referring again to FIG. 1 (enlarged for detail). By disregarding poloidal winding 158 and toroidal-axis pick-up winding 191, (also includes filling in poloidal coil space 157), an eddy current probe PSa remains comprising a solid toroid 155x, poly-phase excitation windings 162 and pick-up coil 190. In the basic form poly-excitation windings 162 are two x-y pairs connected to a sine-cosine generator computer programable for ramping the frequency over predetermined ranges. Pick-up coil 190 is wound upon a non-metalic spool which is spatially adjusted within the fringing driving flux disposing the turns of 190 coplanar to driving vector S-N and coaxial to the z-axis for a signal null. As mentioned the poly-phase excitation winding distributions extend circumferentially around (arrows 61) around the entire core 155x.

Z-axis Pick-up Coil Mode

Pick-up coil 190 is wound of many turns (preferrably multiple strands) upon a non-conducting coil form (not shown). By utilizing a high initial permeability tape wound core material such as Supermalloy* 1F and keeping the excitation below saturation there is sufficient integral z-axis inductance to generate the mentioned oscillatory signal build-up.

Toroidal-axis Pick-up Mode

Again a solid toroid core is wound with poly-phase excitation distributions for driving combined with the described toroidal-axis pick-up winding 191 provides a simple robust eddy current probe. As mentioned, balanced hemispheres 71Ha, 71Hb, results in a net toroidal circulating flux of zero (signal null). Obviously, this mode may be combined with the described z-axis mode for generating at least two signals.

The 2nd Embodiment

Integral Driving-sensing in an Annular Grooved Toroid

FIG. 2 is an isometric-sectional view showing a portion of annular grooved toroid 255. Poly-phase excitation winding distributions (represented in partial by 262 and arrows 61) extend the circumference of core 255 (excitation source connecting leads not shown). Annular groove 256 extends as an air gap between flanges 256a, 256b, into poloidal space 257. Multi-purpose coil 258 is wound within (during tape winding of core 255) poloidal space 257. For coplanarity adjustment of winding 258 a non-conducting spool (not shown) is used having small non-conducting rods 202 attached and extending between turns of winding 262. Rods 202 may be cut off after coplanarity adjustment and winding 258 is rigidly glued in place. Pick-up coil 290 is wound upon a non-conducting spool (not shown) and adjusted for coplanarity (plane of coil 290 perpendicular to the z-axis and may be glued in place also. A cylindrical conducting (copper) case 295 concentrically surrounds core 255 and coil 290. Thick wall case 295 not only serves a probe housing but also as a flux focusing means. As mentioned, winding 158, 258 has multi-modes of utility, first as a pick-up coil and second as a driving field eccentricity generator.

The 3rd Embodiment

Integral Orbital Driving Field Mode

Looking again at FIG. 1, and deleting annular groove 156, if we apply a DC voltage to poloidal winding 158 via leads Ld a poloidal-axis flux 71P flows inducing concentric dipoles n-s on the annular sensing face 143. Concentric dipoles n-s effectively shift the hemispherical driving field (solid arc 71Ha) off center to dashed arc 71Hb. This off-center shifting has an orbital effect on the resultant driving hemisphere as shown by the orbital dashed arrows ORB around the z-axis. Poloidal winding 158 excitation may take the form of a static DC voltage or a spectrum of AC frequencies, preferrably a sub-harmonic of the sine-cosine excitation frequency.

A primary use of this third embodiment is inspection of aircraft splice joints. Exact centering of a probe coaxially to a screw has been time-consuming and unreliable. A poloidal winding within the cross-section of a toroid provides a means for dynamic eccentric shifting the sensing pattern so as to correct axes (probe/screw) mis-alignment. It is contemplated the host computer (lap-top preferred) read the polar coordinates (phase-amplitude) of the z-axis signal applying a predetermined algorithm to generate a correction signal to the poloidal winding 158. A circuit for implementing this corrective action is illustrated by block diagram in FIG. 4. Composite signal SIG.a (the mentioned subharmonic with driving frequency component) from pick-up coil 190 is amplified in amplifier Oa1 and fed to digital processor 113 in turn fed to output amplifier Oa2. The output signal is fed to poloidal winding 158. Example feedback signals are SIG.b, (sine) and SIG.c (triangular).

The 4th Embodiment

Concentric Driving-sensing Toroids

FIG. 3, is a perspective-sectional view of a quadrant of sensor PSc disposing driving-sensing toroids 355a, 355b concentrically with pick-up coils 390a, 390b. Toroid 355a is excited with poly-phase winding distributions 362a extending cumferentially (symbolized by arrows 61a). Toroid 355b also is wound with poly-phase excitation winding distributions 362b (extending the full cumference as indicated by arrows 61b). Interposed concentrically between toroids 355a, 355b is pick-up coil 390a. Around the outside of toroid 355b is wound pick-up coil 390b.

A thick copper flat washer 395 is concentrically disposed around the toroid-pick-up assembly for focusing the driving fields (this type of washer may be utilized with the other embodiments also. Computerized excitation generators control the individual angular velocities of the plurality of driving toroids 355a, 355b for inducing interposed radii eddy current patterns in the workpiece. This embodiment would be of particular utility in imaging sub-surface cracks in aircraft structures.

Further Utility

The global nature of the fringing fields (hemispheres 71Ha, 71Hb) either side of the disclosed devices may by used for sensing and the toroid/torus window 153 may be fitted with a magnifying lens with cross-hairs for centering on an aircraft rivet.

We claim:

1. A toroidal plane sensing face eddy current probe for detecting a flaw in a conducting workpiece by means of detecting an asymmetry in a rotating hemispherical driving field, said probe comprising:
   a) a toroidal core formed of a high permeability material for conducting a diameter-wise rotating field;
      i) poly-phase excitation winding distributions wound through the toroid window to symmetrically cover the core surface;
      ii) ramping poly-phase excitation currents being applied to the said excitation winding distributions for inducing a rotating driving dipole, fringing from the toroidal plane and forming complementary hemispheres of effective flux for inducing a hemispherical eddy current pattern in said workpiece;
      iii) a first pick-up coil wound coaxially around the circumference of the toroid core disposing the pick-up turns coplanar to the said driving dipole for generating a signal null in proximity to a flawless workpiece, net flux linkage to the first pick-up coil being dependent on an asymmetry in the said eddy current pattern for generating a first flaw signal;
      iv) said first pick-up coil shunted by a variable capacitor to form an oscillatory tank circuit for building up a resultant accumulative signal being a sub-harmonic of the said ramping poly-phase excitation currents;
      v) a second pick-up coil of many turns wound toroidally around the said toroid core, the spacing between adjacent turns being uniform for a signal null, said second pick-up coil for detecting an asymmetry in the said eddy current pattern.

2. A toroidal plane sensing face eddy current probe for detecting a crack near a rivet in an aircraft splice joint, providing dynamic alignment of a hemispherical driving field axis with the said rivet axis by means of a predetermined algorithm correction current flowing through a poloidal coil, said probe comprising:
   a) a torus core formed of a high permeability material including a poloidal coil space for conducting both a diameter-wise rotating field and a poloidal axis field from the said toroidal plane to the said splice joint;
   b) poly-phase excitation winding distributions being wound through the torus core window symmetrically cover the torus surface;
      i) poly-phase current from a digital synthesis generator being applied to the said poly-phase excitation winding distributions for inducing the said diameter-wise rotating field fringing from the said toroidal plane in the form of the said hemispherical driving field for coupling to the said aircraft splice joint;
      ii) the said poloidal coil being wound within the said torus core for inducing a poloidal axis field, fringing from the toroidal plane as two concentric annular unlike magnetic poles;
      iii) the said diameter-wise rotating field and the said poloidal axis field vectorially adding across the sensing face for eccentrically shifting the axis of the hemispherical driving field in response to the said predetermined algorithm correction current;
   c) a first pick-up coil having many turns concentrically wound around the torus core for generating a first signal in response to an asymmetry in the said hemispherical driving field;
      i) a variable capacitor connected across the first pick-up coil for resonant tuning;
   d) a second pick-up coil having many turns wound toroidally around the said torus core for generating a second signal in response to an asymmetry in the said hemispherical driving field;
      i) a variable capacitor connected across the second pick-up coil for resonant tuning;
   e) the said predetermined algorithm correction current being generated by a digital processor responding to alignment feedback derived from the said first and second signals.

3. The invention of claim 2, wherein the said torus core is formed with an annular groove extending axially from the said poloidal coil space to the core surface taking the form of a pot-core half.

4. An eddy current probe utilizing concentrically disposed driving-sensing toroids, said probe comprising:
   a) at least two toroid cores formed of a high permeability material;
      i) each of the said at least two toroid cores being toroidally wound with poly-phase excitation winding distributions;
      ii) each of the said wound toroid cores being driven by a computerized poly-phase excitation generator connected to the said poly-phase winding distributions for independently controlling the angular velocity of the resultant diameter-wise driving dipole fringing hemispherically from the plane of each of the said toroid cores for coupling to a conducting workpiece;
   b) the concentric diameter-wise driving dipoles inducing an interposed radii of concentric eddy current patterns in the workpiece having predetermined angular velocities, and hemispherical flux depths;
      iii) a pick-up coil of many turns interposed concentrically between the said driving-sensing toroids, the pick-up coil turns being coplaner to the said driving-sensing toroids for a signal null, said pick-up coil for detecting an asymmetry in the said eddy current patterns;
      iv) an additional pick-up coil of many turns disposed concentrically around the outermost driving-sensing toroid radius for detecting an asymmetry in the said eddy current patterns.

* * * * *